United States Patent [19]

Kostic et al.

[11] Patent Number: 5,352,771
[45] Date of Patent: Oct. 4, 1994

[54] HYDROLYSIS OF PEPTIDE BONDS USING PT (II) AND PD (II) COMPLEXES

[75] Inventors: Nenad M. Kostic; Longgen Zhu, both of Ames, Iowa

[73] Assignee: Iowa State University Research Foundation Inc., Ames, Iowa

[21] Appl. No.: 938,436

[22] Filed: Aug. 31, 1992

[51] Int. Cl.$^5$ .......................... C07K 1/12; C07K 3/10
[52] U.S. Cl. .................................... 530/345; 530/343
[58] Field of Search ................ 514/492; 530/333, 343, 530/345; 424/646, 649, 617

[56] References Cited

U.S. PATENT DOCUMENTS

| | | | |
|---|---|---|---|
| 4,584,392 | 4/1986 | Smith et al. | 556/137 |
| 4,783,482 | 11/1988 | Amundsen et al. | 514/492 |
| 4,870,160 | 9/1989 | Charonis et al. | 530/326 |
| 5,019,646 | 5/1991 | Furcht et al. | 530/326 |
| 5,059,425 | 10/1991 | Tsilibary et al. | 424/445 |
| 5,112,945 | 5/1992 | Westermark et al. | 530/324 |

OTHER PUBLICATIONS

Wilson et al., Inorg. Chem. 9, 528 (1970).
S. Benkovic et al., "The Enzymic Nature of Antibody Catalysis: Development of Multistep Kinetic Processing", *Science*, 250:1135 (1990).
R. Bose, "Kinetics and Mechanisms of Platinum(II)–Promoted Hydrolysis of Inorganic Polyphosphates", *Inorg. Chem.*, 24:3989 (1985).
I. Burgeson et al., "Selective Hydrolysis of PeptideBonds, Catalyzed by the Platinum Complexes Attached to the Amino-Acid Side Chains", The Third Chemical Congress of North America in Toronto (Jun. 1988)), *Inorg.* Abstract 31 (1988).
I. Burgeson et al., "Selective Peptidase and Protease Activity of Platinum Complexes", 197th National Meeting of the American Chemical Society in Dallas, Tex. (Apr. 1989)), *Inorg.* Abstract No. 61 (1989).
I. Burgeson et al., "Selective Hydrolysis of Peptides and Proteins Promoted by Platinum Complexes", 198th National Meeting of the American Chemical Society in Miami (Sep. 1989)), *Inorg.* Abstract No. 24 (1989).
I. Burgeson et al., "Selective Hydrolysis of Unactivated Peptide Bonds, Promoted by Platinum(II) Complexes Anchored to Amino Acid Side Chains", *Inorg. Chem.*, 30:4299 (1991).
J. Chin et al., "Developing Artificial Hydrolytic Metalloenzymes by a Unified Mechanistic Approach", *Acc. Chem. Res.*, 24:145 (1991).
M. De Rosch et al., "Hydrolysis of Phosphodiesters with Ni(II), Cu(II), Zn(II), Pd(II), and Pt(II) Complexes", *Inorg. Chem.*, 29:2409 (1990).
M. Ermacora et al., "Conformation-Dependent Cleavage of Staphylococcal Nuclease with a Disulfide-linked Iron Chelate", *Proc. Natl. Acad. Sci.*, 89:6383 (1992).
A. Fersht, *Enzyme Structure and Mechanism*, 2nd edition, at pp. 405–425, W. H. Freeman & Co. (N.Y.), publisher (1985).
R. Hay et al., "Metal Ion Promoted Hydrolysis of Amino Acid Esters and Peptides" in *Metal Ions in Biological Systems*, 5:173–243 (1976), Marcel Dekker, Inc. (N.Y.), publisher.
D. Kahne et al., "Hydrolysis of a Peptide Bond in Neutral Water", *J. Am. Chem. Soc.*, 110:7529 (1988).
R. Kluger et al., "Carboxylic Acid Participation in (List continued on next page.)

Primary Examiner—Merrell C. Cashion, Jr.
Assistant Examiner—Sheela J. Huff
Attorney, Agent, or Firm—Warren D. Woessner

[57] ABSTRACT

The present invention provides a method for the selective cleavage of peptide amide bonds under ambient conditions by treating a peptide comprising the subunit —CO—NH—CH((CH$_2$)$_x$SY)CONH— wherein x is 1-2 and Y is H or (C$_1$–C$_4$)alkyl in an aqueous medium with a tetracoordinate Pd(II) or tetracoordinate Pt(II) complex which promotes the hydrolysis of the adjacent amide bond proximal to the carboxy terminus of the subunit.

16 Claims, 5 Drawing Sheets

OTHER PUBLICATIONS

Amide Hydrolysis: Competition Between Acid-Catalyzed Dehydration and Anhydride Formation", *J. Am. Chem. Soc.*, 111:5921 (1989).

F. Menger et al., "Origin of Rate Accelerations in an Enzyme Model: The p-Nitrophenyl Ester Syndrome", *J. Am. Chem. Soc.*, 109:3145 (1987).

T. Rana et al., "Specific Cleavage of a Protein by an Attached Iron Chelate", *J. Am. Chem. Soc.*, 112:2457 (1990).

T. Rana et al., "Iron Chelate Mediated Proteolysis: Protein Structure Dependence", *J. Am. Chem. Soc.*, 113:1859 (1990).

T. Rana et al., "Transfer of Oxygen from an Artificial Protease to Peptide Carbon During Proteolysis", *Proc. Natl. Acad. Sci.-USA*, 88:10578 (1991).

D. Satchell et al., "Kinetic Studies of Metal Ion Catalysis of Heterolytic Reactions", *Annu. Rev. Prog. Chem., Sect. A: Phys. Inorg. Chem.*, 75:25 (1978).

J. Suh, "Model Studies of Metalloenzymes Involving Metal Ions as Lewis Acid Catalysts", *Acc. Chem. Res.*, 25:273 (1992).

P. Sutton et al., "Cobalt(III)-Promoted Hydrolysis of Amino Acid Esters and Peptides and the Synthesis of Small Peptides", *Acc. Chem. Res.*, 20:357 (1987).

GSH

GSSG

GSMe

γ-Glu-Met-Gly

α-Glu-Met-Gly hydrolysis of the amide bond

HYDROLYSIS OF PEPTIDE BONDS USING PT (II) AND PD (II) COMPLEXES

This invention was made with government support under Grant CHE 88-58387, awarded by the National Science Foundation. The U.S. Government has certain rights in the invention.

BACKGROUND OF THE INVENTION

The fundamental structural units of peptides are α-amino acids, about 20 of which are the building units for all proteins. All amino acids except the simplest one, glycine, are capable of existing in both D and L configurations with respect to their α-carbon, but naturally occurring proteins contain only the L-enantiomers. Peptides are dimers, oligomers, or long-chain polymers (polypeptides) which formally result from the condensation of the amino acids to thus produce amide (commonly called peptide or peptidyl) linkages, —CONH—.

Hydrolysis of proteins and peptides has been studied more from the biochemical than from the chemical point of view, but the mechanisms at the molecular level of these important reactions remain largely obscure. As reported by D. Kahne et al., *J. Amer. Chem. Soc.*, 110, 7529 (1988), the half-life for hydrolysis of the amide bond in neutral aqueous solution is about 7 years. Even with the strongest acids or bases in high concentrations, prolonged heating is necessary. Because of this extreme unreactivity, kinetic and mechanistic studies have been done almost exclusively with amides that are variously activated by substituents, by ring strain, by forced nonplanarity, or by proximate functional groups. For example, see R. Kluger et al., *J. Amer. Chem. Soc.*, 111, 5921 (1989); ibid., 101., 6976 (1979). Moreover, the reaction mixtures usually are heated to promote cleavage.

However, proteolytic enzymes, such as chymotrypsin, hydrolyze even unactivated amide bonds rapidly under mild conditions. For example, see A. Fersht, *Enzyme Structure and Mechanism*, Freeman, N.Y. (2d ed. 1985) at pages 405–425. Although some biomimetic systems surpass chymotrypsin in the rate of stoichiometric hydrolysis of activated esters, these systems fall short of enzymes, which are true catalysts and which hydrolyze even unactivated amides. See, F. M. Menger et al., *J. Amer. Chem. Soc.*, 109, 3145 (1987). Catalytic antibodies hold promise for enzyme-like hydrolysis of peptides because these agents are true catalysts and because they show selectivity. For example, see S. Benkovic et al., *Science*, 2.50, 1135 (1990).

Since certain proteolytic enzymes are known to require metal ions for activity, ester hydrolysis has been attempted using various metal complexes. However, carboxylic and phosphate esters are used as substrates more often than amides. For example, see R. W. Hay et al., in *Metal Ions in Biological Systems*, Vol. 5, H. Sigel, ed., Marcel Dekker, N.Y. (1976) at page 173 and D. P. N. Satchell et al., *Annu. Rev. Prog. Chem., Sect. A: Phys. Inorq. Chem.*, 75, 25 (1978). Complexes of cobalt(III) and of copper(II) have been studied more than any other, and mechanisms by which these metal ions act are known in detail. See, P. A. Sutton et al., *Acc. Chem. Rec.*, 20, 357 (1987) (Co(III)) and J. Chin, *Acc. Chem. Res.*, 24, 145 (1991) (Co(III) and Cu(II)). Since cobalt-(III) complexes bind to the N-terminal amino-acid residue of peptides, only the N-terminal amide bond in the peptide is hydrolyzed. Although these reactions are stoichiometric, they are relevant to turnover reactions catalyzed by aminopeptidases. Recent reports of oxidative cleavage of proteins mediated by metal complexes widen the range of inorganic methodologies for accomplishing these biochemical reactions. For example, see T. M. Rana et al., *J. Amer. Chem. Soc.*, 112, 2457 (1990), ibid., 113, 1859 (1990); T. M. Rana et al., *PNAS USA*, 88, 10578 (1991).

Platinum(II) complexes have been used previously to promote hydrolysis of inorganic oligophosphates and of activated phosphate esters. For example, see R. N. Bose et al., *Inorg. Chem.*, 24, 3989 (1985) and M. A. De Rosch et al., *Inorg. Chem.*, 29, 2409 (1990). However, a continuing need exists for methods to selectively hydrolyze peptide bonds under mild conditions.

SUMMARY OF THE INVENTION

BRIEF DESCRIPTION OF THE INVENTION

The present invention provides a method for peptide bond cleavage comprising reacting a peptide comprising a subunit of the formula (I):

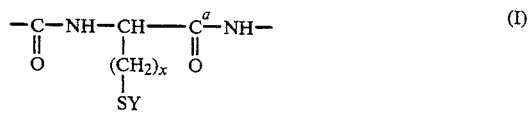

Wherein x is 1 or 2 and Y is H or $(C_1-C_4)$alkyl, in an aqueous medium, with an amount of a tetracoordinate Pt(II) complex or a Pd(II) complex, wherein said complex comprises four chloro ligands or 1–3 $H_2O$ (aqua) ligands, which complex is effective to bind to the SY unit of subunit I and to hydrolyze the amide bond designated (a), proximal to the carboxy terminus of said subunit, to yield the corresponding free acid ($—CO_2H$) and amine ($H_2N—$). Preferably, Y is H or $CH_3$, and the mole ratio of the Pt(II) or Pd(II) complex to the subunit of formula (I) is about 1:1. Of course, if the peptide contains a plurality of subunits of formula (I), the amount of total Pt(II) complex and/or Pd(II) complex that is used can be adjusted to promote the hydrolysis of each of the subunit amide bonds proximal to the carboxyl terminus of the subunit.

Except as specifically noted hereinbelow, the present method is general to any peptide, including proteins, oligopeptides and polypeptides, either naturally-occurring or synthetic, that comprise at least one subunit of formula (I). Also, except as specifically noted hereinbelow, the nature of the Pt(II) or Pd(II) complex is not critical, so long as it can (a) bind to the SY unit in subunit (I), and hydrolyze the adjacent amide bond (a) in an aqueous reaction medium.

Thus, the present invention provides a method for nonenzymatic, selective cleavage of peptide bonds, in which suitable coordination complexes selectively bind to sulfur atoms in the side chains of the peptidyl residues methionine, cysteine, and S-alkyl cysteine and selectively promote cleavage of peptide bonds adjacent to the anchoring sulfur-containing residues. For example, platinum(II) complexes proved capable of promoting, under relatively mild conditions, the hydrolysis of unactivated amide bonds in peptides and in other amino-acid derivatives. When the substrates and platinum(II) promoters were matched so as to aid hydrolysis, the reaction half-lives fell in the range from 2 days to 2 hr at 40° C. With $[Pd(H_2O)_3(OH)]^+$ as the promoter, the reaction half-lives in some cases are measured in minutes.

The present method is useful, for example, to isolate the region responsible for bioactivity in a given peptide or protein, such as those disclosed hereinbelow, or in any other amino acid sequence in which the location of a subunit of formula I is known. The present method can also be used to determine whether a peptide comprises a subunit of the formula I, i.e., methionine, cysteine or S-alkylcysteine.

As used herein with respect to the peptide substrates, the term "hydrolyze" refers both to the ability of the sulfur-bound metal complexes to directly hydrolyze the adjacent amide bond by internal transfer of an $H_2O$ molecule from the metal to the amide group and to the ability of the metal to promote attack on the amide group with an exogenous $H_2O$ molecule from the aqueous reaction medium. (See FIG. 4).

As depicted, the subunit of formula (I) is depicted in accord with conventional peptide nomenclature, wherein the amino-terminus of the peptide is to the left of formula I and the carboxy terminus of the peptide is to the right.

DETAILED DESCRIPTION OF THE INVENTION

Peptides

Figure 1:
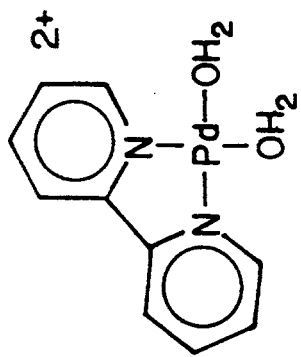
FIG. 1 depicts the structural formulas of certain Pt(II) and Pd(II) complexes useful in the present method.
Figure 1:
Figure 1:
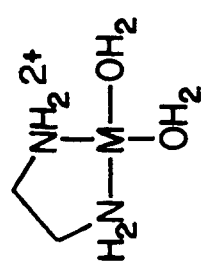
Figure 1:
Figure 1:
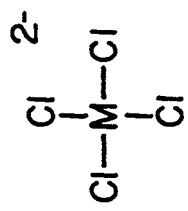
Figure 1:
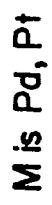
Figure 1:
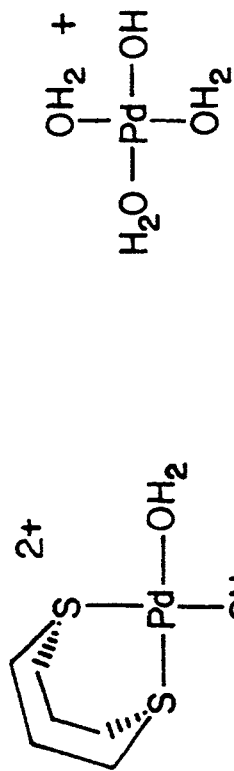
Figure 1:
Figure 1:
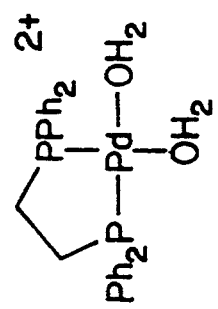
Figure 1:

A wide variety Of naturally-occurring and synthetic peptides, including proteins, polypeptides and oligopeptides (dipeptides, tripeptides, tetrapeptides, etc.) can be hydrolyzed in accord with the present method, as long as they comprise at least one subunit of the formula (I). The subunit of formula (I) can also be substituted in the alpha-position or on the side chain by substituents which do not substantially interfere with the binding of the metal complex, e.g., with ($C_1$–$C_5$)alkyl, ($C_1$–$C_{10}$)aryl, e.g., phenyl, tolyl, anisyl, xylyl and the like and ($C_1$–$C_5$)alkoxy.

The present method may be employed to cleave both the simple proteins and conjugated proteins. Simple proteins include the naturally-occurring proteins which yield only alpha-amino acids or their derivatives on hydrolysis. They are of several types and include:

(a) Albumins, which are soluble in water and coagulated by heat; e.g., ovalbumin in egg white and serum albumin in blood.

(b) Globulins, which are insoluble in water but soluble in dilute salt solutions and coagulable by heat; e.g., serum globulin in blood, purified antibody preparations, including monoclonal antibodies, fragments of monoclonal antibodies including recombinant mammalian binding regions, i.e., chimeric murine-human antibodies.

(c) Glutelins, which are insoluble in water or dilute salt solution but soluble in dilute acid and alkali; e.g., glutenin in wheat.

(d) Prolamines, which are insoluble in neutral solutions but soluble in 80% alcohol; e.g., zein in corn and gliadin in wheat.

(e) Albuminoids, which are dissolved only by boiling in strong acids; e.g., keratins in hair and horny tissue, elastins in tendons and arteries, and collagens in skin and tendons.

(f) Histones, which are basic in reaction, soluble in water but insoluble in dilute ammonia, and difficultly heat-coagulable; e.g., thymus histone.

(g) Protamines, which are strongly basic in reaction and soluble in water, dilute acid, and ammonia; e.g., salmin and sturin in fish sperm.

Conjugated proteins include those proteins which are combined with some nonprotein substance. The classes include:

(a) Phosphoproteins—contain a phosphoric acid moiety as the prosthetic group, e.g., casein in milk and ovovitellin in egg yolk.

(b) Nucleoproteins—the nonprotein portion is a nucleic acid; el.g., nuclein in cell nuclei.

(c) Glycoproteins—simple proteins united to a carbohydrate group; e.g., mucins in vitreous humor and saliva, lectins in plants, viral glycoproteins, such as HIV, HCMV and HBV glycoproteins, and erythropoietin.

(d) Chromoproteins—contain a colored prosthetic group; e.g., hemoglobin in blood, and flavoproteins.

(e) Lipoproteins—proteins in combination with lipid materials such as sterols, fatty acids, lecithin, etc. These include lipoprotein a, high-density lipoprotein cholesterol (HDL-cholesterol) and low-density lipoprotein cholesterol (LDL-C).

(f) Metalloproteins—the prosthetic group contains a metal; e.g., enzymes such as tyrosinase, arginase, xanthine oxidase, and non-enzymes such as hemoglobin.

(g) Fusion proteins, which are hybrids of different proteins obtained by methods of genetic engineering.

Enzymes are polypeptides which may be classified under six general groups: hydrolases, oxidoreductases, transferases, lyases, isomerases, and ligases. The first group, hydrolase enzymes, include proteolytic enzymes, which hydrolyze proteins, e.g., elastase, papain, ficin, pepsin, trypsin, chymotrypsin, bromelin, and keratinase; carbohydrases, which hydrolyze esters, e.g., lipase, choloinesterase, lecithinase, and phosphatase; nucleases, that hydrolyze nucleic acid, e.g., ribonuclease and deoxyribonuclease; and amidases, which hydrolyze amines, e.g., arginase, asparaginase, glutaminase, and urease. The second group are redox enzymes, which catalyze oxidation or reduction reactions. These include glucose oxidase, catalase, peroxidase, lipoxidase, and cytochromes. The third group are transferase enzymes, which transfer groups from one molecule to another. Examples of these are glutamic-pyruvic transaminase, glutamic-oxalacetic transaminase, transmethylase, phosphopyruvic transphosphorylase, and dehydrogenase. The fourth group are lyase enzymes, which catalyze the cleavage of C-C, C-O, C-N and other bonds by elimination, leaving double bonds, or conversely, adding groups to double bonds. Examples of these are pyruvate decarboxylase, amino acid decarboxylase, aldolase, fumarate hydratases, aconitate hydratases, and ammonia lyase. The fifth group are isomerase enzymes, which catalyze the dehydrogenation and epimerization of amino acids and sugars. An example of an isomerase is phosphoglucomutase. The sixth group are ligase enzymes, which catalyze the synthetic linking of two molecules, simultaneously with the breakdown of ATP. Examples of these are aminoacyl-tRNA synthetases and biotinyl-dependent carboxylases.

Chemotactic peptides, which are involved in the mechanisms of chemoattraction, can also be cleaved, e.g., the monocyte attractor, N-formyl-Met-Leu-Phe-benzyl ester. See, P. P. Ho et al., *Arthritis Rheum.*, 21, 133 (1978). Immunomodulators and mammalian cell growth factors can also be cleaved in accord with the invention. They include lymphokines, such as the interleukins, and the hematopoietic growth factors such as colony-stimulating factor, GM-CSF, M-CSF, G-CSF, ED-CSF, MCGF and the like. See, *Hematopoiesis*, D. W. Golde, Ed., Churchill Livingstone, N.Y. (1984) at pages 203–244.

The polypeptide hormones can also be cleaved in accord with the present method. These include the pituitary, parathyroid, and pancreatic hormones. Pituitary hormones include growth hormone releasing factor, somatotropin or human growth hormone, somatostatin, follicle-stimulating hormone, luteinizing hormone, human chorionic gonadotropin, thyrotropin, corticotropin (ACTH,) hypothalamic hormone, and the like. Pancreatic hormones include pancreatic glucagon, insulin, amylin, and pancreastatin.

The endorphins, e.g., α-endorphin and β-endorphin, can also be cleaved using the present methods, as can neuropeptide K and methionine-containing enkephalin analogs such as proenkephalin. A number of the gastrointestinal peptides can also be cleaved. They include gastrin-related peptide, gastrin-related tetrapeptide (N-t-Boc-Trp-Met-Asp-Phe-amide), (SEQID NO:1) carerulein, galanin message associated peptide (1–41), motilin, gastric inhibitory polypeptide, gastrin I, minigastrin I, gastrin releasing peptide, vasoactive intestinal peptide (porcine), and the like.

Other bioactive peptides useful as substrates include melanocyte stimulating hormones, opioid peptides such as adrenal peptide E and bovide adrenal medulla docosapeptide, oxytocin, isotocin, vasopressin, conotoxin, endothelin, epidermal growth factor brain natriuretic peptide, magainin I, magainin II, molluscan excitatory peptide, molluscan cardioexcitatory neuropeptide, transforming growth factor-α, α-SK-2-mating factor and urotensin.

Bioactive subunit peptides, which are formally subunits of these proteins and polypeptides, may also be cleaved using the method of the invention. These include, inter alia, polypeptides with fibronectin activity (see U.S. Pat. No. 5,019,646), polypeptides with Type IV collagen activity (see U.S. Pat. No. 5,059,425), polypeptides with laminin activity (see U.S. Pat. No. 4,870,160), islet amyloid polypeptide subunits (see U.S. Pat. No. 5,112,945), fragments of adrenocorticotropic hormone (e.g., 4–10), endorphin fragments, epidermal growth factor fragments (e.g., 1–53), and fragments of human growth hormone releasing factor (1–40; 1–29).

For a more extensive listing of bioactive peptides comprising methionine and/or cysteine residues, including literature citations, see *ICN Biochemicals Catalog*, ICN Biomedicals, Inc., Irvine, Calif. (May 1992-1993) at pages 985–1030, and *Biochemicals and Organic Compounds for Research and Diagnostic Reagents*, Sigma Chemical Co., St. Louis (1989) at pages 282–325.

Pt(II) and Pd(II) Complexes

Pt(II) and Pd(II) complexes useful as hydrolysis promoters in the present method are tetracoordinate coordination or organometallic complexes of negative, neutral or positive net charge, i.e., $-2, 0, +1$ or $+2$, preferably with halo, aqua, thio and amino ligands. Preferred complexes are $[PdCl_4]^{2-}$, $[PtCl_4]^{2-}$, $[(H_2O)_3PdOH]^{+1}$ or complexes of the general formula $[(L)_2M(H_2O)_2]^{+2}$ wherein M is Pd or Pt, each L is a two electron donor, e.g., chloride ion, or an organic molecule comprising a nitrogen, sulfur or phosphorous atom, such as an amine, phosphine, cyanide, isocyanide, or sulfide. Preferably, the moiety $(L)_2$ is a diamino-, diphosphino- or a dithia-substituted aliphatic, cycloaliphatic or aromatic ligand, including 1,ω-alkylenediamine, i.e., ethylenediamine; 2′,2′-bipyridine; 1,ω-diphenylphosphinylalkane, i.e., 1,2-(diphenylphosphinyl)ethane, or a dithiacycloalkane, i.e., 1,5-dithiacyclooctane. Other useful Pd(II) and Pt(II) complexes include pyrrole-2-carboxylic acid and 2-thiophene-carboxylic acid.

As exemplified hereinbelow, complexes of the formula $[(L)_2M(H_2O)_2]^{+2}$ can be readily prepared from the corresponding compounds of the formula $(L)_2MCl_2$, many of which are commercially available, by reaction of the chloride complex with an aqueous solution of at least two equivalents of a monovalent metal salt. To hydrolyze peptides, an amount of the Pd(II) or Pt(II) promoter complex is simply mixed with the peptide in a mole ratio of complex to subunit(s) of formula I desired to be hydrolyzed of about 1:1 in an aqueous medium (e.g., water or deuterium oxide) at ambient temperatures (e.g., 20°–40° C.) for a period of time effective to complete the hydrolysis. The preferred pH range is discussed in detail in Example 7, below.

The invention will be further described by reference to the following detailed examples wherein the water was distilled, demineralized and purified to a resistance greater than 10MΩ.cm. The deuterium-containing compounds $D_2O$, $DClO_4$, and NaOD and the complexes $K_2[PdCl_4]$, $K_2[PtCl_4]$, and cis-[Pt(en)Cl$_2$] were obtained from Sigma Chemical Co., St. Louis, Mo. Anhydrous $AgClO_4$ was obtained from G. Frederick Smith Chemical Co. All other chemicals were of reagent grade.

Proton NMR spectra at 300 MHz of solutions in $D_2O$ were recorded with a Varian VXR300 spectrometer, with DSS as an internal reference. The sample temperature was kept constant within ±0.1° C. Infrared spectra of mulls were recorded with an IBM98 Fourier-transform spectrometer. Photoacoustic infrared and far infrared spectra were recorded with a Perkin-Elmer FTIR 1800 spectrometer and an MTEC 200 photoacoustic detector. A spectrum of carbon black was recorded between the sample spectra in order to normalize variations owing to the infrared source and to the spectrometer. Ultraviolet-visible spectra were recorded with an IBM 9430 spectrophotometer, whose monochromator has two gratings. The pH was measured with a Fischer 925 instrument and a Phoenix Ag/AgCl reference electrode. The uncorrected values in deuteriated solvents are designated pH*. Elemental analyses were done by Galbraith Laboratories, Inc.

To evaluate the stability of nonmetallated substrates, solutions of amino-acid derivatives and peptides were prepared as in the hydrolysis examples, below, except that the metal complexes were not added. The solvent always was $D_2O$ and pH* was adjusted with $DClO_4$ or NaOD. In some experiments $AgClO_4$ was added as well. The solutions were kept at 40°±1° C. and occasionally examined by $^1H$ NMR spectroscopy. Only about 10% of AcMet-Gly hydrolyzed, with liberation of glycine, over 12 d at pH* 0.70.

Free glycine, one of the hydrolysis products, was identified by $^1H$ NMR spectroscopy and by thin-layer chromatography. Addition of pure glycine to the reaction mixture enhanced the $^1H$ NMR signal of the hydrolysis product, and no new signal appeared.

Reactions for analysis by thin-layer chromatography were run for 6 hr at 50° C., so that hydrolysis was complete. The metal complex was precipitated out by addition of diethyldithiocarbamate, and the yellow solid was removed by filtration. The colorless filtrate was chromatographed on silica gel G with a mixture of n-butanol, acetic acid, and water in the volume ratio 40:6:15 and developed with a solution containing 300 mg of ninhydrin in a mixture of 3 mL of glacial acetic acid and 100 mL of n-butanol. A control solution containing glycine instead of the hydrolysis substrate was treated exactly like the reaction mixture. Both the reaction mixture and the control solution yielded a single spot with an $R_f$ value of 0.202.

EXAMPLE 1

Preparation of Metal Complexes

The palladium (Pd) and platinum (Pt) complexes tested as hydrolysis promoters are depicted in FIG. 1, and their composition formulas (abbreviated names) are given below the structural formulas. The following chloro complexes were prepared by published procedures: cis-[Pd(en)$Cl_2$] was prepared as disclosed by H. Hohmann et al., *Inor. Chim. Acta*, 174, 87 (1990); cis-[Pd(bpy)$Cl_2$] was prepared as disclosed by G. B. Kauffman, in *Inorg. Synthesis*, Vol. VII, J. Kleinberg, ed., McGraw-Hill, N.Y. (1963) at page 249. Cis-[Pd(dppe)$Cl_2$] was prepared as disclosed by J. A. Davies et al., *J. Chem. Soc., Dalton Trans.*, 2246 (1980). The complex trans-[$PtCl_2(H_2O)_2$] is the nominal precursor of the complex trans-[$PtCl_2(H_2O)$(GSMe)]+, which was obtained by treating [$PtCl_3$(GSMe)] with Ag+ ions in aqueous solution.

The corresponding complexes with aqua or $D_2O$ ligands were obtained by treating each of these three complexes with two equivalents of anhydrous $AgClO_4$, in $D_2O$ as the solvent, as disclosed by G. Mehal et al., *Inorg. Chem.*, 24, 4165 (1985). However, hereinbelow, the complexes will be depicted as comprising $H_2O$ and −OH ligands for the sake of clarity. The complex [$Pd(H_2O)_3$-(OH)]$ClO_4$ in solution was obtained by stirring a mixture of $K_2$[$PdCl_4$] and four equivalents of anhydrous $AgClO_4$ in $D_2O$ for 4 hr at 35° C. The pH* (uncorrected for isotope effect) was adjusted to 1.0 by addition of $DClO_4$. Control experiments showed that $AgClO_4$ itself does not promote hydrolysis of substrates. On the basis of the $pK_a$ value for the process in eq. 1:

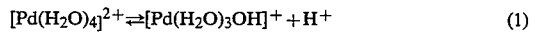

$$[Pd(H_2O)_4]^{2+} \rightleftharpoons [Pd(H_2O)_3OH]^+ + H^+ \quad (1)$$

it is believed that the complex [$Pd(H_2O)_3OH$]+ is the main species present at a pH of about 1.0. Since amine, phosphine, or thio ether ligands are good electron donors, the heteroleptic aqua complexes in FIG. 1 are less acidic than the homoleptic aqua complex in Equation 1.

These heteroleptic complexes exist mainly in the fully protonated forms under the hydrolysis conditions, and their formulas are written accordingly.

The complex cis-[Pd(dtco)($H_2O$)$_2$]($ClO_4$)$_2$, containing the ligand 1,5-dithiacyclooctane, was prepared in solution at pH* 2.0 by the procedure of C. Drexler et al., *Inorg. Chem.*, 30, 1297 (1991). In each case the solid AgCl was removed by filtration in the dark, and a fresh solution of the aqua complex was used in further experiments.

The aqua complexes in solution were characterized by UV-vis and $^1H$ NMR spectroscopic methods. For cis-[Pd(en)($H_2O$)$_2$]($ClO_4$)$_2$, $\epsilon = 260-276$ M$^{-1}$cm$^{-1}$ at 340–345 nm and $\delta_{en} = 2.63$ ppm (s); the UV-vis spectrum is consistent with the values reported by H. Hohmann et al., cited above. For cis-[Pd(bpy)($H_2O$)$_2$]($ClO_4$)$_2$, $\epsilon = 2020$ M$^{-1}$cm$^{-1}$ at 310 nm and $\delta_{bpy} = 7.71$, 8.31 ppm (both m). For cis-[Pd(dppe)($H_2O$)$_2$]$ClO_4$)$_2$, there are no peaks in the UV-vis region; $\delta_{CH_2} = 2.86$, 3.00 ppm (both m); $\delta_{C_6H_5} = 7.66$, 7.84, 7.89 ppm (all m). For [Pd($H_2O$)$_3$-(OH)]$ClO_4 \delta = 90-120$ M$^{-1}$ cm$^{31\ 1}$ at 390–400 nm; these values are close to those reported for the complex [Pd($H_2O$)$_3$Cl]+ by L. I. Elding et al., *Inorg. Chim. Acta*, 20, 65 (1976).

EXAMPLE 2

Preparation of Amino-Acid Derivatives and Peptides

Figure 2:
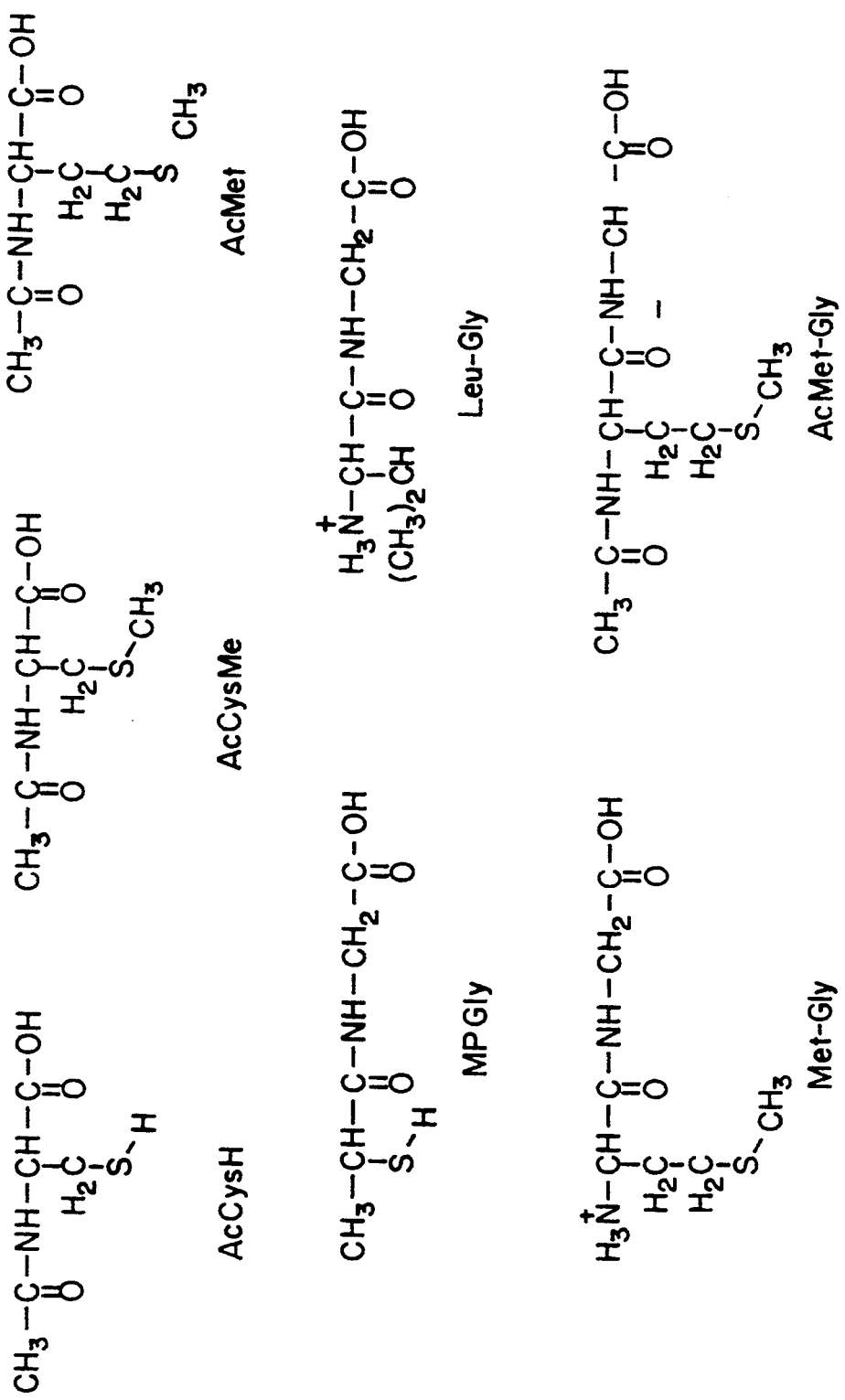
FIG. 2 depicts the structural formulas of certain peptides which can be hydrolyzed in accord with the present method.
Figure 2A:
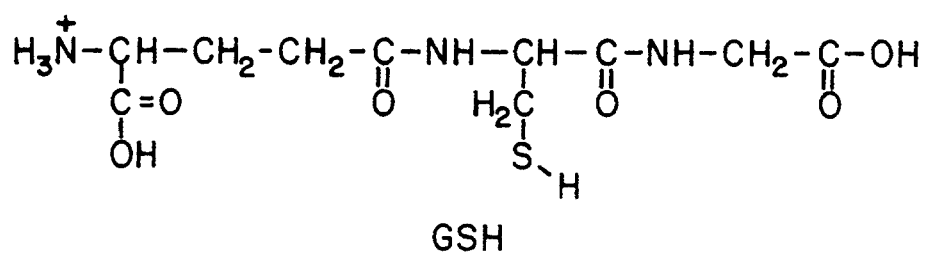
Figure 2A:
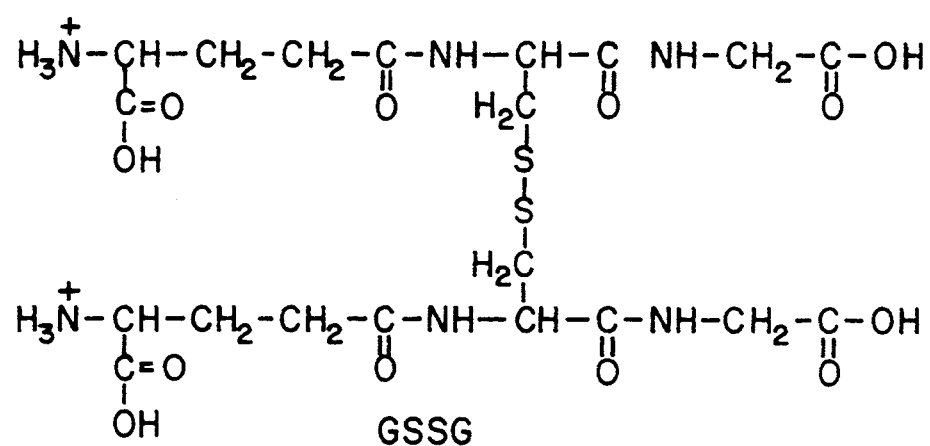
Figure 2A:
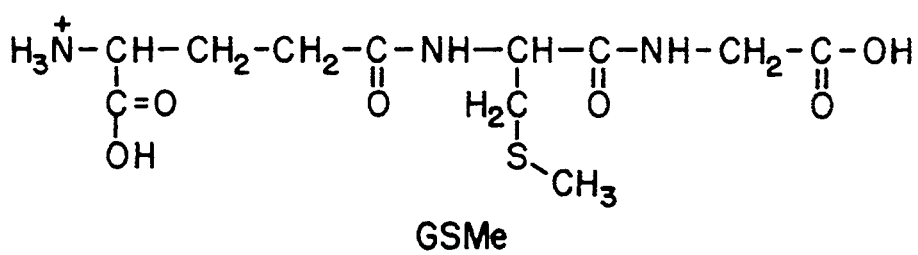
Figure 2A:
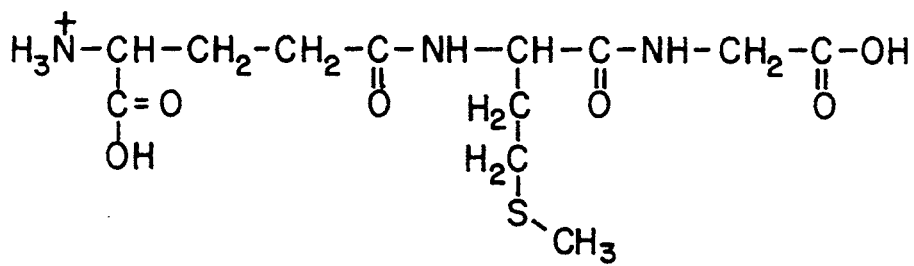
Figure 2A:
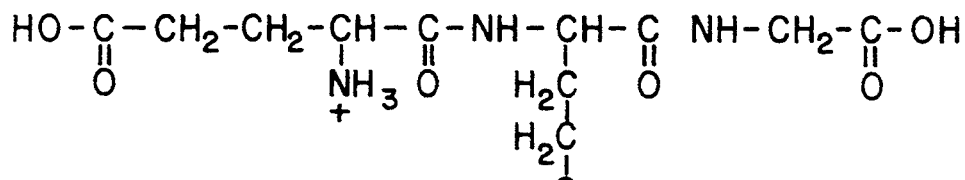

Amino-acid derivatives and peptides hydrolyzed in accord with the present invention are depicted in FIG. 2, and their abbreviated names are given below the formulas. Their charges are as expected for major species at pH 2.0. Glycine (Gly), S-methyl-L-cysteine (CysMe), N-acetyl-L-cysteine (AcCysH), N-(2-mercaptopropionyl)-glycine (MPGly), N-acetylmethionine (AcMet), methionylglycine (Met-Gly), leucylglycine (Leu-Gly), reduced glutathione (GSH), S-methylglutathione (GSMe), and oxidized glutathione (GSSG) were obtained from Sigma Chemical Co. The tripeptides α-Glu-Met-Gly and Y-Glu-Met-Gly were synthesized by the standard solid-state method and purified by HPLC in the Protein Facility at Iowa State University. The compound N-acetyl-S-methyl-DL-cysteine (AcCysMe) was prepared as disclosed by G. P. Wheeler et al., *J. Amer. Chem. Soc.*, 73, 4604 (1951).

The peptide N-acetylmethionylglycine (AcMet-Gly) was obtained by adding acetic anhydride (58.8 μL, 0.64 mmol) to a stirred solution of Met-Gly (128 mg, 0.64 mmol) in 1.60 mL of glacial acetic acid and stirring at 35° C. for 3 hr. Evaporation of the reaction mixture in vacuo at 40° C. yielded a white powder; $^1H$ NMR data (δ values): 2.05, s, $CH_3CO$; 2.11, s, $CH_3S$; 4.00, s, Gly $CH_2$.

EXAMPLE 3

Attachment of Metal Complexes to Amino-Acid Side Chains

Substrates and the freshly prepared metal complexes, shown in FIGS. 1 and 2, were mixed pairwise, in equimolar amounts in 150 μl $D_2O$ to a final concentration of 50 mM of each. Reactions were followed by $^1H$ NMR spectroscopy at 40° C. In some experiments, ternary mixtures of cis-[Pd(dtco)($H_2O$)$_2$]$^{2+}$, amino-acid derivative or peptide, and thiourea(tu) were studied. A mixture of this complex, AcMet, and thiourea in the mole ratio 1:1:2 yields the precipitate cis-[Pd(dtco)(tu)$_2$]$^{2+}$, and free AcMet remains in solution. A mixture in the mole ratio 1:1:1 contains cis-[Pd(dtco)(AcMet)(tu)]$^{2+}$. All of these experiments were done at pH* 0.99.

glutathione is converted into a complex of the structure:

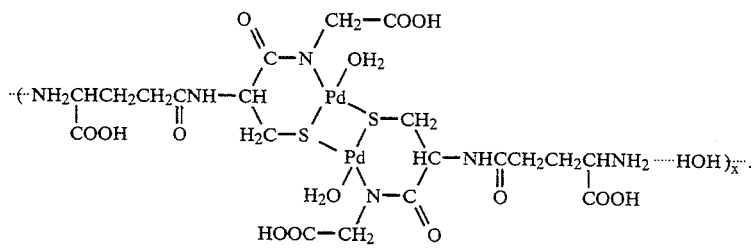

Initial attachment of the promoter to the substrate amounts to displacement of a chloro or aqua ligand by the thiolate or thio ether group in the side chain. This displacement is accompanied by a characteristic shift downfield of the CH$_3$S $^1$H NMR resonance (in the case of thio ethers) as shown by the data on Table 1, below.

TABLE 1

Effect of Coordination on $^1$H NMR Chemical Shifts ($\delta$, in ppm) of CH$_3$S Groups at pH* = 1.0$^a$

| promoter$^b$ | Active form | GSMe | AcMet-Gly |
|---|---|---|---|
| none | | 2.13 | 2.11 |
| [PtCl$_4$]$^{2-}$ | mononuclear | 2.44 | 2.35 |
| [PdCl$_4$]$^{2-}$ | mononuclear | 2.35 | 2.28 |
| [Pd(H$_2$O)$_3$(OH)]$^+$ | mononuclear | 2.26, 2.28 | 2.29 |
| | binuclear | 2.41 | 2.47 |
| cis-[Pd(en)(H$_2$O)$_2$]$^{2+}$ | mononuclear | 2.26, 2.28 | 2.37 |
| | binuclear | 2.44 | 2.50 |
| cis-[Pd(dtco)(H$_2$O)$_2$]$^{2+}$ | mononuclear | | 2.37 |
| | binuclear | | 2.50 |

$^a$Uncorrected for isotope effect.
$^b$Since the solvent is D$_2$O, exchangeable H atoms are deuteriated.

EXAMPLE 4

Preparation of [Pd(GS)(H$_2$O)]$_2$.H$_2$O

Upon addition of 0,255 g (0,830 mmol) of reduced glutathione to an equimolar amount of cis-[Pd(en)(H$_2$O)$_2$](ClO$_4$)$_2$ in 5.0 mL H$_2$O solution at pH 2.0, the color turned red, and a yellow-orange precipitate subsequently formed. This solid was filtered, washed with ethanol and acetone, and dried in vacuo overnight. Infrared spectrum ($\nu$in cm$^{-1}$) of free GSH: 3340 and 3250, NH$_3^+$ and NH$_2$; 2524, SH; 1710, COOH; 1610, COO$^-$ asym; and 1394, COO$^-$ sym. Infrared spectrum ($\nu$in cm$^{-1}$) of [Pd(GS)(H$_2$O)]$_2$.H$_2$O: 3510, H$_2$O; 3244 and 3066, NH$_2$; 1753, COOH; 1526, NH$_2$; 1638, COO$^-$ asym; 1384, COO$^-$ sym; 564, Pd-N; 412, Pd-O; and 382, Pd-S. Analysis; calculated (found) for C$_{20}$H$_{36}$N$_6$O$_{15}$S$_2$Pd$_2$: C, 27.38 (27.45); H, 4.14 (4.17); N, 9.58 (9.45).

The reaction in eq. 2 differs from most of the others because it yields an insoluble product with the composition [Pd(GS)(H$_2$O)$_2$]$_2$.H$_2$O.

2GSH + 2[Pd(en)(H$_2$O)$_2$]$^{2+}$ + H$_2$O → [Pd(GS)(H$_2$O)$_2$]$_2$.H$_2$O + 2 enH$_2$$^{2+}$ (2)

The palladium-ligand stretching vibrations in it were assigned according to the values provided by L. D. Pettit et al., *Coord. Chem. Rev.*, 61, 97 (1985). The infrared spectra, elemental analysis, and insolubility in several common solvents are consistent with the polymeric structure shown below. The S-H vibrational band disappears, and the Pd-S, Pd-N, and Pd-O bands appear, as Since the COOH band in the complex is shifted by only 38 cm$^{-1}$ from its position in free glutathione, this group is not coordinated to palladium. The $^1$H NMR resonance of the glycine CH$_2$ group is shifted upfield, to 2.74 ppm; this is a clear sign of coordination of amide group to palladium(II) via deprotonated nitrogen atom. Such coordination under the pH values and other reaction conditions used in this study is well documented, e.g., by S. Kasselauri et al., *Coord. Chem. Rev.*, 104, 1 (1990). So is the formation of stable thiolate bridges between palladium(II) atoms. See, for example, I. Sovago et al., *J. Inorg. Nucl. Chem.*, 43, 425 (1981).

EXAMPLE 5

Figure 3:
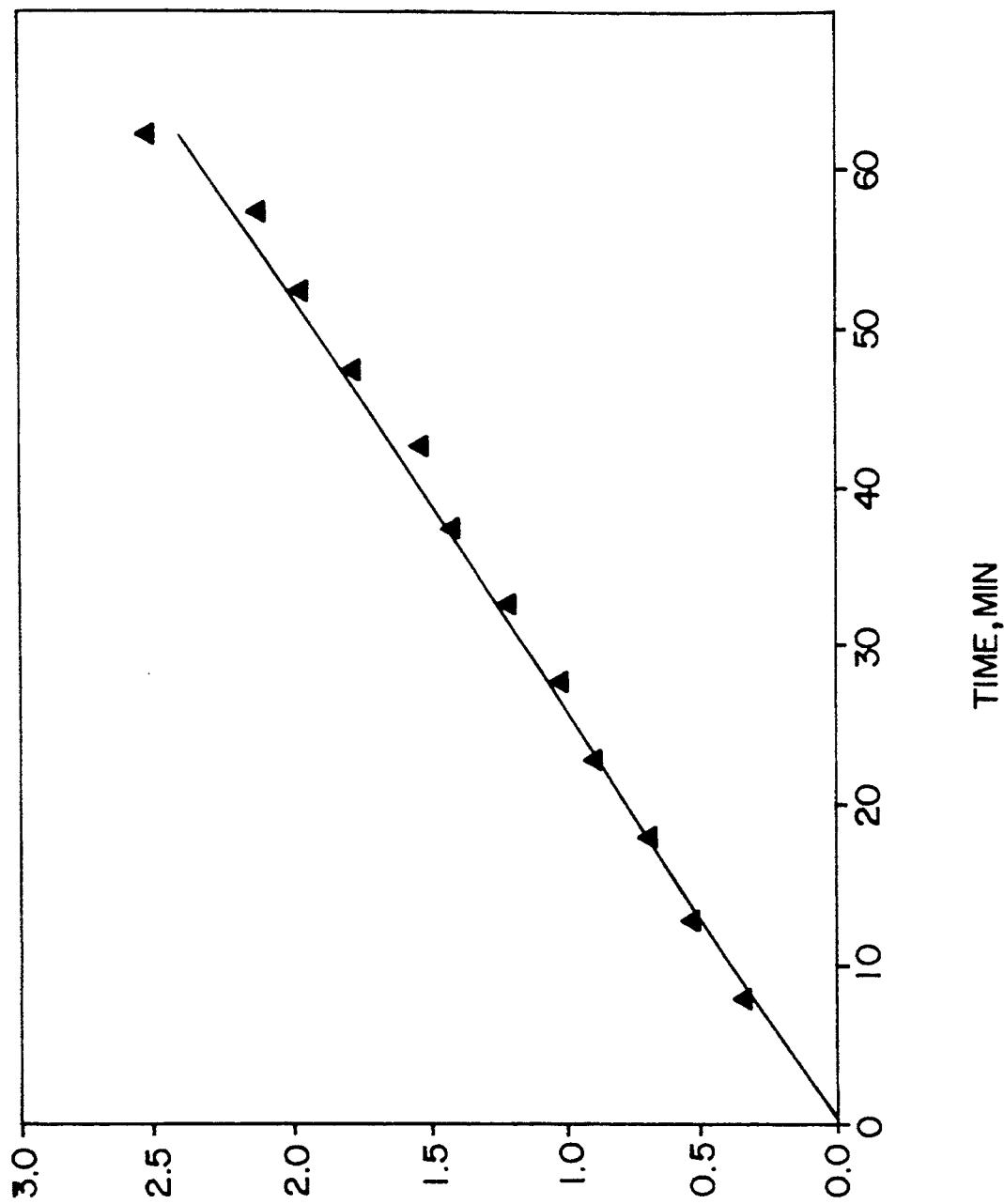
FIG. 3 depicts a first-order kinetic plot for hydrolysis of the methionine-glycine amide bond in N-acetylmethionylglycine, promoted by deuteriated cis-[Pd(en)(-$H_2O)_2]^{2+}$ in $D_2O$, at pH* 1.00 (uncorrected for the isotope effect), and $50\pm0.1°$ C.

Hydrolysis of S-Methylglutathione (GSMe), Promoted by Pt(II) and Pd(II) Complexes Equimolar amounts of GSMe and of a freshly prepared metal aqua complex, both dissolved in D$_2$O, were mixed rapidly in an NMR tube. The solution was 50.0 mM in each, and the volume was 600 μL. Acquisition of the $^1$H NMR spectra began as soon as possible, and 16 scans were taken at each time. The temperature was kept within ±0.1° C. of the nominal value of 40° C. The pH* value was measured before and after the hydrolysis reaction; the difference was less than 0.10, and the final value is reported on Table II. The methylene signals of free glycine and of peptide-bound glycine were integrated with errors estimated at ±5%. Concentrations of these two forms of glycine were calculated on the basis of the signal areas and the known initial concentration of the substrate. First-order logarithmic plots of substrate concentration or of free glycine concentration versus time were linear for three half-lives (FIG. 3). Slow hydrolysis reactions were followed for less than three half-lives. Typical plots consisted of 10–20 points, and correlation coefficients were 0.980–0.996. Enthalpies and entropies of activation, ΔH++ and ΔS++, were calculated by Eyring equation. Their error bounds were computed by a standard method. (K. B. Wiberg et al., *Physical Organic Chemistry*, Wiley: N.Y. (2d ed. 1964) at page 379 ).

TABLE II

Hydrolysis of the Cysteine-Glycine Bond in S-Methylglutathione, Promoted by Complexes of Palladium(II) and Platinum(II)

| promoter$^a$ | pH*$^b$ | 10$^6$k$_{obsd}$, min$^{-1}$ at 40° C. |
|---|---|---|
| [PdCl$_4$]$^{2-}$ | 1.20 | 220 ± 10 |
| cis-[Pd(en)(H$_2$O)$_2$]$^{2+}$ | 0.97 | 300 ± 10 |
| [Pd(H$_2$O)$_3$(OH)]$^+$ | 0.83 | 850 ± 10 |
| cis-[Pd(bpy)(H$_2$O)$_2$]$^{2+}$ | 0.88 | 7.3 ± 0.8 |
| [PtCl$_4$]$^{2-}$ | 1.10 | 2700 ± 100 |

TABLE II-continued

Hydrolysis of the Cysteine-Glycine Bond in S-Methylglutathione, Promoted by Complexes of Palladium(II) and Platinum(II)

| promoter[a] | pH*[b] | $10^6 k_{obsd}$, min$^{-1}$ at 40° C. |
|---|---|---|
| cis-[Pt(en)(H$_2$O)$_2$]$^{2+}$ | 0.97 | 610 ± 40 |

[a]See Table I, footnote b.
[b]See Table I, footnote a.

The data on Table II demonstrate that various complexes of divalent palladium and platinum promote selective hydrolysis of the cysteine-glycine bond (eq 3) under conditions at which free S-methylglutathione is completely stable for weeks.

$$H_3\overset{+}{N}-CH-CH_2-CH_2-C-NH-CH-C-NH-CH_2-COOH + H_2O + H^+ \longrightarrow \quad (3)$$

with substituents COOH, O, H$_2$C, O, and S—M—/H$_3$C $$H_3\overset{+}{N}-CH-CH_2-CH_2-C-NH-CH-COOH + H_3\overset{+}{N}-CH_2-COOH$$

with substituents COOH, O, H$_2$C, and S—M—/H$_3$C

The complex cis-[Pd(dppe)(H$_2$O)$_2$]$^{2+}$ produced a white precipitate with this peptide, and hydrolysis was not detected (dppe=bis(diphenylphosphino)ethylene). For this substrate, platinum(II) complexes are better promoters than palladium(II) complexes. The fastest of these reactions, the one promoted by [PtCl$_4$]$^{2-}$, has a half life of 4.3 hr.

EXAMPLE 6

Hydrolysis of N-Acetylmethionylglycine (AcMet-Gly), Promoted by Pt(II) and Pd(II) Complexes The yellow precipitate formed upon mixing of the dipeptide Met-Gly and [PdCl$_4$]$^{2-}$ as K$_2$PdCl$_4$ in D$_2$O (150 μl) at a concentration of 50.0 mM each is the stable S,N-bidentate complex. (V. Theodorou et al., *Polyhedron*, 4, 1283 (1985)). When, however, the amino group of the methionyl residue is acetylated, the metal-containing promoter complexes bind solely to the sulfur atom, and hydrolysis reactions proceed smoothly as shown in eq 4.

$$CH_3-C-NH-CH-C-NH-CH_2-COOH + \quad (4)$$

with substituents O, H$_2$C, H$_2$C, S—M—/H$_3$C $$H_2O + H^+ \longrightarrow CH_3-C-NH-CH-COOH +$$

with substituents O, H$_2$C, H$_2$C, S—M—/H$_3$C $$H_3\overset{+}{N}-CH_2-COOH$$

The data of Table III demonstrate that various complexes promote hydrolysis of the methionine-glycine amide bond in AcMet-Gly.

TABLE III

Hydrolysis of the Methionine-Glycine Bond in N-Acetylmethionylglycine, Promoted by Complexes of Palladium(II) and Platinum(II)

| promoter[a] | pH*[b] | $10^6 k_{obsd}$, min$^{-1}$ at 40° C. |
|---|---|---|
| [PdCl$_4$]$^{2-}$ | 1.14 | 5.1 ± 0.1 |
| cis-[Pd(en)(H$_2$O)$_2$]$^{2+}$ | 1.00 | 140 ± 20 |
| [Pd(H$_2$O)$_3$(OH)]$^+$ | 1.07 | 260 ± 30 |
| [PtCl$_4$]$^{2-}$ | 1.09 | 15 ± 1 |
| cis-[Pt(en)(H$_2$O)$_2$]$^{2+}$ | 0.94 | 4.6 ± 0.6 |

[a]See Table I, footnote b.
[b]See Table I, footnote a.

A typical kinetic plot for the hydrolysis with cis-[Pd(en)H$_2$O)$_2$] is shown in FIG. 3. Thiourea (tu) inhibits the hydrolysis reaction, and this effect was studied in reactions involving cis-[Pd(dtco)H$_2$O)$_2$]$^{2+}$. Kinetic results are given in Table IV, below.

TABLE IV

Hydrolysis of the Methionine-Glycine Bond in N-Acetylmethionylglycine, Promoted by cis-[Pd(dtco)(H$_2$O)$_2$]$^{2+a}$ in the Presence of Thiourea

| mole ratio Pd:substrate:tu | pH*[b] | $10^3 k_{obsd}$, min$^{-1}$ at 50° C. |
|---|---|---|
| 1:1:1 | 0.99 | 0 |
| 1:0.5:0 | 1.09 | 11 ± 1 |
| 1:1:0 | 1.00 | 3.1 ± 0.5 |
| 1:0.5:0.5 | 0.99 | 0.7 ± 0.2 |

[a]See Table I, footnote b.
[b]See Table I, footnote a.

Generally speaking, hydrolysis of AcMet-Gly is promoted more efficiently by palladium(II) complexes than by platinum(II) complexes. The fastest reaction observed has the half-life of less than 30 min.

EXAMPLE 7

Hydrolysis of Different Substrates, Promoted by [PdCl$_4$]$^{2-}$

K$_2$[PdCl$_4$] and the substrates listed on Table V were mixed in equimolar amounts in 150 μl D$_2$O to a final concentration of 50.0 mM each. As Table V shows, the rate at which glycine is released varies considerably among different substrates. Unlike the other substrates, which contain the amide bond on the carboxylic side of the methionine or cysteine anchoring group and release glycine, AcCysMe contains only an amide bond on the amino side of the cysteine anchor and therefore releases acetic acid.

TABLE V

Hydrolysis in Various Substrates, Promoted by $[PdCl_4]^{2-}$

| substrate[a] | pH*[b] | $10^6 k_{obsd}$, min$^{-1}$ at 40° C. |
|---|---|---|
| GSMe | 1.20 | 220 ± 10 |
| GSH | 0.79 | 12.5 ± 0.6 |
| AcMet-Gly | 1.14 | 510 ± 10 |
| GSSG | 0.81 | 114 ± 13 |
| MPGly | 0.65 | very low |
| AcCysMe | 0.81 | 1.6 ± 0.2 |

[a]The first five substrates release glycine; the last one releases acetic acid.
[b]See Table I, footnote a.

EXAMPLE 8

Dependence of Hydrolysis Rate on pH

In this study the effect of pH was examined with the substrates AcMet-Gly and Y-Glu-Met-Gly and with the promoter $[Pd(H_2O)_3(OH)]^+$. The former reaction is shown in eq 4, and the latter is analogous to it. The results as shown in Table VI, below.

TABLE VI

Effect of pH on Hydrolysis of the Methionine-Glycine Bond in Two Peptides, Promoted by $[Pd(H_2O)_3(OH)]^{+a}$

| substrate | pH*[b] | $10^2 k_{obsd}$, min$^{-1}$ at 40° C. |
|---|---|---|
| AcMet-Gly | 1.07 | 2.6 ± 0.3 |
|  | 1.05 | 2.8 ± 0.1 |
|  | 0.95 | 4.2 ± 0.1 |
|  | 0.88 | 5.0 ± 0.1 |
|  | 0.68 | 7.1 ± 0.3 |
|  | 0.53 | 8.5 ± 0.1 |
| γ-Glu-Met-Gly | 1.20 | 1.5 ± 0.1 |
|  | 0.82 | 3.8 ± 0.1 |
|  | 0.49 | 6.9 ± 0.1 |

[a]See Table I, footnote b.
[b]See Table I, footnote a.

The effect of pH was also examined with the substrate S-methylglutathione (GSMe) and with two platinum(II) complexes, $[PtCl_4]^{-2}$ and trans-$[PtCl_2(H_2O)_2]$ (nominally, see Example 1), as promoters. The synthetic peptide Y-Glu-Met-Gly used is homologous to S-methylglutathione; the two substrates differ only in one methylene group in the anchoring side chain (methionine versus S-methylcysteine). The rate constants in this and the previous study obey the linear equations in Table VII. The reactions promoted by $[Pd-(H_2O)_3-(OH)]^+$, for which the slope is greater than 0.90, depend on pH more than the reactions promoted by platinum(II) complexes, for which the slope is only ca. 0.10.

TABLE VII

Relationships Between pH*[a] and the Rate Constant for Hydrolysis of the Amide Bond Involving Glycine in Peptides, Promoted by Palladium(II) and Platinum(II) Complexes at 40° C.

| substrate | promoter[b] | log $k_{obsd}$ = |
|---|---|---|
| AcMet-Gly | $[Pd(H_2O)_3(OH)]^+$ | −0.53 − 0.94 pH* |
| γ-Glu-Met-Gly | $[Pd(H_2O)_3(OH)]^+$ | −0.69 − 0.93 pH* |
| GsMe | $[ptCl_4]^{2-}$ | −2.5 − 0.098 pH* |
|  | trans-$[PtCl_2(H_2O)_2]$ | −2.3 − 0.11 pH* |

[a]See Table I, footnote a.
[b]See Table I, footnote b.
[c]See the explanation in Example 1.

EXAMPLE 9

Hydrolysis of Cytochrome c, Promoted by Pd(II) Complexes

A mixture containing 1.0 mg of horse-heart cytochrome c (Type II, Sigma Chem. Co.) and 0,036 mg of cis[Pd(en)(H$_2$O)$_2$](BF$_4$)$_2$(mole ratio of 1:1) in 60 μl of 0.10M aqueous solution of HBF$_4$ was incubated at 40°±1° C. for two days. The complex cis-[Pd(en)(-H$_2$O)$_2$](BF$_4$)$_2$ was obtained by treating cis-[pd(en)Cl$_2$] with two equivalents of anhydrous AgBF$_4$ in H$_2$O. The reaction was quenched by addition of 1.0 μl of a 0.20M aqueous solution of diethyldithiocarbamic acid. The mixture was stored at −20° C. before it was analyzed. To 30 μl of the thawed hydrolyzate mixture were added 30 μl of a 0.200M solution of Na$_2$HPO$_4$ so that the final pH was 6. After addition of 240 μl of the SDS reducing buffer, the solution was heated at 95° C. for 4 min. After cooling, the yellow precipitate of palladium(II)/diethyldithiocarbamate was removed by centrifugation. Electrophoresis was done with an 18% running gel, in a Protean II minigel apparatus by Bio-Rad, Inc. Presence of bands whose molecular mass is lower than that of cytochrome c is an evidence of protein cleavage into peptides. The number of these peptides is determined by the number of cleavage sites in the original protein. The electrophoretic pattern therefore indicates the degree of selectivity in protein cleavage.

We examined the dependence of the cleavage reaction on the acid (HClO$_4$, HBF$_4$, and HCOOH), on the choice of the Pd(II)promoter, on the mole ratio of the Pd(II)promoter to the protein, and on the incubation time. The temperature was kept at 40° C. When the mole ratio is from 0.5 to 2.0 and incubation time is from 1 to 6 days, cleavage is selective.

Discussion

Consideration of the substrates in FIG. 2 reveals what structural features of the peptide are required for hydrolysis. The dipeptide Leu-Gly does not hydrolyze in the presence of metal complexes because it lacks a side chain that can coordinate to the metal atom. Substrates that can form stable chelates with the intended promoter do not hydrolyze, either. For example, as discussed above, the dipeptide Met-Gly forms an insoluble S,N-bidentate complex with palladium(II), while its N-acetylated derivative (AcMet-Gly) hydrolyses with loss of glycine. Similarly, the tripeptide α-Glu-Met-Gly forms an insoluble S,N,N-tridentate complex, while its isomer Y-Glu-Met-Gly hydrolyses with loss of glycine. The amide nitrogen atom of methionine coordinates to the palladium(II) atom only when this coordination yields a tridentate chelate (in α-Glu-Met-Gly), but does not coordinate when the product would be merely a bidentate chelate (in Y-Glu-Met-Gly).

The single attachment of the promoter to the subunit(I) (S-Pd or S-Pt) is a distinctive feature of the use of these platinum(II) and palladium(II) complexes for the cleavage of peptides. Since these two metals have high affinity for sulfur ligands, they bind selectively to side chains of cysteine (or S-methylcysteine) and of methionine and activate only the amide bonds adjacent to these anchors. However, the anchoring side chain must also be sufficiently long to allow approach of the metal complex to the target amide bond. As Tables II-V show, the substrate MPGly, in which the —SH anchoring group is directly bonded to the main amino acid chain, hydrolyses in the presence of palladium(II) complexes much more slowly than substrates in which the anchoring group is at the terminus of an aminoacid methylene or ethylene side chain.

The interaction between the promoter and the target amide bond can be analyzed on the basis of the kinetic results in Tables II and III. The reactions in equations 3 and 4 may follow two competing general pathways, shown in FIG. 4. In the first pathway coordination of the peptide nitrogen atom stabilizes the amide bond involved and thus inhibits its cleavage. In the second pathway, interaction of the metal complex with the carbonyl group can lead to hydrolysis of the CONH bond by two mechanisms. The metal atom may form a chelate with the oxygen atom, further polarizing the $C=O$ bond and activating it toward external attack by solvent water. Alternatively, an aqua ligand attached to the metal atom may attack the carbon atom internally, in an efficient intramolecular reaction. The presence of an aqua ligand on the metal complex does not guarantee that this ligand will be internally delivered to the target amide bond; in other words, one of the (unspecified) ligands in the chelation mechanism can be a water molecule. The mechanism via chelation and external attack by water is favored when the side chain permits formation of a favorable ring. This is the case with S-methylglutathione, for which $x=1$ and the chelate ring is six-membered.

The mechanism via internal delivery of an aqua ligand is favored when the side chain permits approach of the metal-aqua fragment to the target amide bond. This is the case with AcMet-Gly and with the $\alpha$ and Y isomers of Glu-Met-Gly, substrates for which $x=2$ and for which therefore the chelate ring would be seven-membered and unfavorable.

Both platinum(II) and palladium(II) complexes selectively promote hydrolysis of the amide bond involving the carboxylic group of the anchoring amino-acid residue, e.g., the amide proximal to the carboxyl terminus of the peptide. Only when such an amide bond is absent, as in AcCysMe, does hydrolysis occur at the amide bond proximal to the amino terminus of the peptide, i.e., at the amide group involving the amino group of the anchoring sulfur-containing peptidyl residue. For example, GSMe and AcCysMe both contain S-methylcysteine as an anchor. As Table V shows, the former substrate hydrolyses about 140 times faster than the latter under similar conditions.

Figure 4:
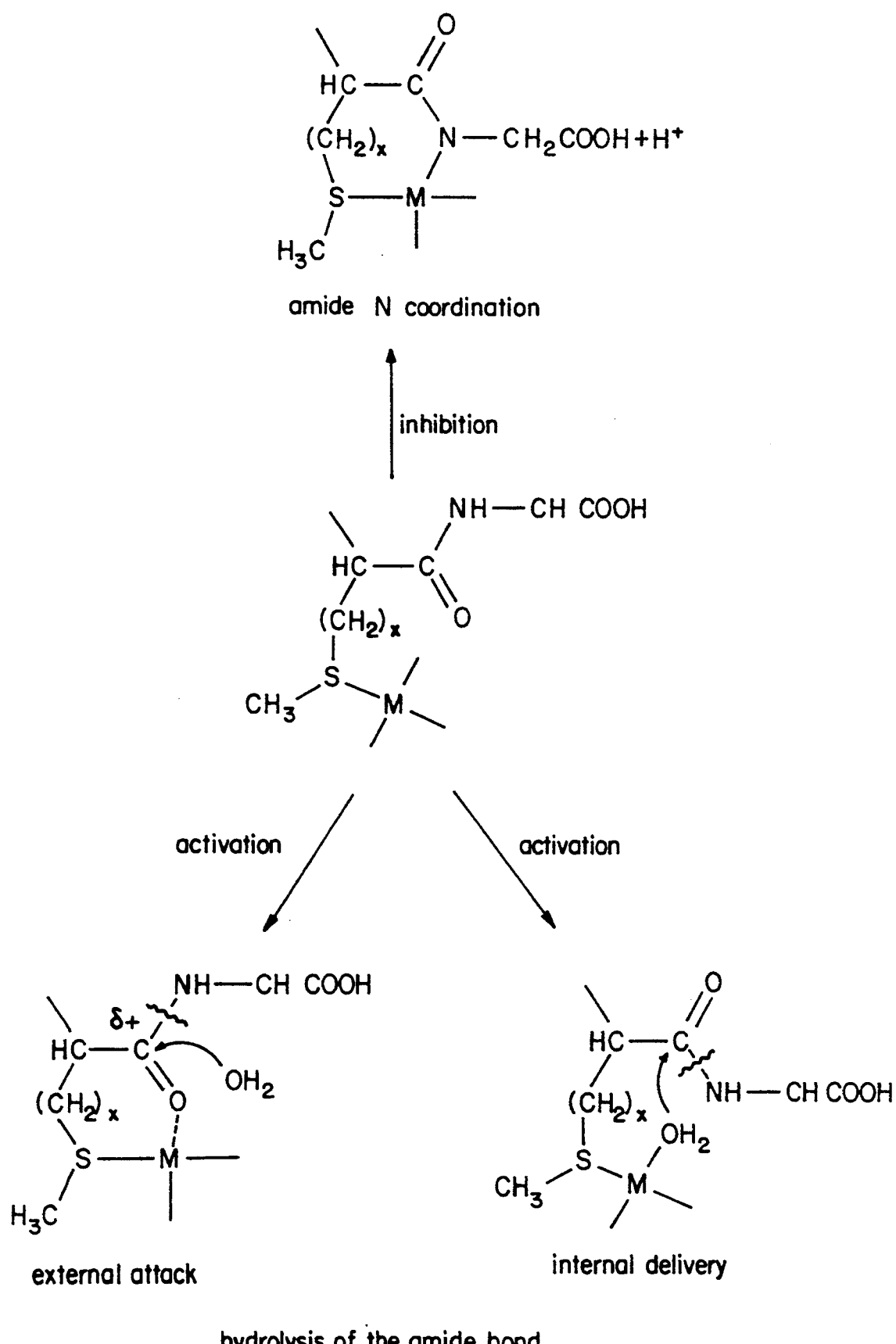
FIG. 4 is a reaction scheme summarizing two proposed mechanisms of action for the present peptide hydrolysis method.

Kinetic findings in Tables II and III can also be explained in terms of FIG. 4. Palladium(II) is more effective than platinum(II) in assisting deprotonation of amides. Pd(II) binds to the amide nitrogen atom even at low pH values. Therefore hydrolysis of GSMe (eq 3), in which the inhibition pathway is stereochemically feasible, is promoted more efficiently by platinum(II) complexes than by analogous palladium(II) complexes. Palladium(II) complexes are labile, whereas platinum(II) complexes are inert to loss of ligands (such as water). Therefore hydrolysis of AcMet-Gly (eq 4), in which the mechanism of internal delivery is stereochemically feasible, is promoted more efficiently by palladium(II) complexes than by analogous platinum(II) complexes.

Similar peptide substrates differing in the length of the side chain apparently can hydrolyze by different mechanisms and similar complexes differing in the nature of the divalent metal atom promote hydrolysis by different mechanisms.

The $^1H$ NMR spectra monitored during hydrolysis indicate that the main active forms of $[PtCl_4]^{2-}$ and of the Pd(II) promoters are mononuclear complexes, as shown in FIG. 4. The unspecified ligands are chloride ions and/or water molecules. When, however, the promoter is added as a preformed aqua complex, the changes in the $^1H$ NMR signal of the $CH_3S$ group are characteristic of the binuclear complex shown schematically below. Most of the examples described below were done with $[Pd(H_2O)_3(OH)]^+$; in this case the unspecified ligands are aqua and hydroxo ligands.

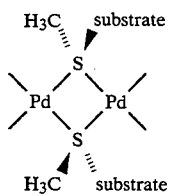

The mechanism shown in FIG. 4 still applies to experiments using $[Pd(H_2O)_3(OH)]^+$, except that each formula shows only one half of the actual substrate-promoter complex. Since the aqua ligands in the binuclear complex are positioned cis to the substrate molecules, water can be delivered to the target amide bond. Since the aqua ligands are positioned trans to the thio ether ligands, the palladium-oxygen bonds are labile. This combination of stereochemical and kinetic properties makes binuclear complexes more efficient than mononuclear complexes in promoting hydrolysis. In the binuclear active complex formed from $[Pd(H_2O)_3(OH)]^+$ there is at least one aqua ligand, and possibly two of them, in the cis position to each substrate (peptide), available for hydrolysis, Therefore the reactions promoted by $[Pd(H_2O)_3(OH)]^+$ are particularly fast.

Since thiourea is more nucleophilic than the methionine side chain (a thio ether) toward palladium(II), mononuclear and binuclear complexes are were easily prepared in solution by mixing the following three compounds in various molar proportions: cis-$[Pd(dtco)(H_2O)_2]^{2+}$, AcMet or AcMet-Gly, and thiourea. The resulting complexes were detected and quantitated owing to the characteristic $^1H$ NMR resonances, listed in Table I, of the methylthio group in terminal and bridging positions. Kinetic results are given in Table IV. When the mole ratio is 1:1:1, the complex cis-$[Pd(dtco)(AcMet-Gly)(tu)]^{2+}$ is formed, and hydrolysis is not observed. Evidently, an aqua ligand is necessary for hydrolysis reaction. When the mole ratio is 1:0.5:0, there are two possibilities: first, an equimolar mixture of the mononuclear complexes cis-$[Pd(dtco)(AcMet-Gly)(H_2O)]^{2+}$, which contains the peptide as a terminal thio ether ligand, and unspent cis-$[Pd(dtco)(H_2O)_2]^{2+}$; and second, the binuclear complex $[Pd_2(dtco)_2(H_2O)_2(\mu\text{-AcMet-Gly})]^{2+}$, which contains the peptide as a bridging thio ether ligand. Proton NMR spectra show absence of the mononuclear complex and presence of the binuclear one. At this mole ratio, hydrolysis occurs fastest because the binuclear complex contains two aqua ligands in cis positions to the peptide, which are available for internal delivery to the peptide bond. When the mole ratio is 1:1:0, again there are two possibilities: cis-$[Pd(dtco)(AcMet-Gly)(H_2O)]^{2+}$ or $[Pd_2(dtco)_2(\mu\text{-AcMet-Gly})_2]^{2+}$. Again, proton NMR spectra show that only the binuclear complex is present. This kinetic difference rules out the hypothesis that the mononuclear aqua complex cis-[Pd(dtco)(AcMet-Gly)(H₂O)]²⁺ is responsible for hydrolysis at both mole ratios. If it were, the rate constants $k_{obsd}$ for this unimolecular reaction would be equal. Both kinetic and spectroscopic evidence support the notion of the binuclear active complex between the substrate and the promoter.

The complex [Pd₂(dtco)₂(μ-AcMet-Gly)₂]²⁺, formed when the mole ratio is 1:1:0, does not contain aqua ligands, and yet hydrolysis occurs (albeit at a reduced rate). Since proton NMR spectra show the presence of free peptide in solution, the equilibrium in eq 5 exists. Opening of the M₂S₂ rings of this type is well know. The diaqua complex shown in equation (5)

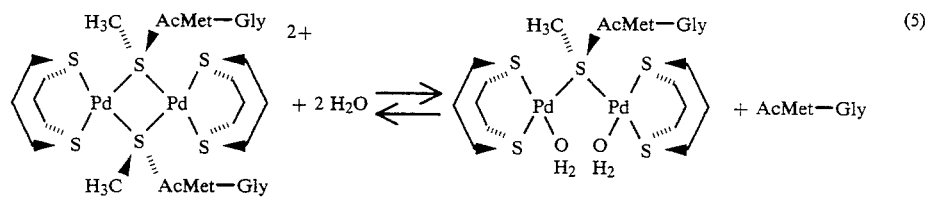

(5)

in this case (at the mole ratio 1:1:0) has two options—recombination with free AcMet-Gly or hydrolysis of the coordinated AcMet-Gly. The diaqua complex in the previous case (at the mole ratio 1:0.5:0) had only the latter option. This explains the fourfold difference between the corresponding rate constants in Table IV.

When the mole ratio is 1:0.5:0.5, ¹H NMR spectroscopy shows bridging coordination of the methione side chain. The other bridging ligand is proposed to be thiourea, as shown below. Although the coordination mode of thiourea is not directly evident from ¹H NMR spectra, it is known to act as a bridging ligand. Since there are

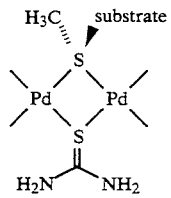

no aqua ligands in the principal form of the complex, hydrolysis depends on the minor forms in which some of the ligands are aquated. Indeed, the rate constant for hydrolysis is only ca. 7% of the optimal value. These reactive, minor forms have escaped detection by ¹H NMR spectroscopy.

As Table VII shows, hydrolysis promoted by platinum(II) complexes depends little on pH (in the relatively narrow range over which this dependence could be studied). This fact is consistent with the mechanism involving rate-limiting chelation step, followed by external attack. The shortness of the anchoring side chain (x=1) in S-methylglutathione favors chelation, and inertness of platinum(II) aqua complexes disfavors internal attack. But hydrolysis promoted by a palladium-(II) complex depends significantly on pH (again in the relatively narrow range near the $pK_a$ value). The observed slope is close to 1.00, the value expected on the basis of eq 6. The agreement between the results in Table VI and the kinetic $$\log k_{obsd} = \log \frac{k_1 k_2}{k_{-1} + k_2} - pH \qquad (6)$$

relationship in eq 6 supports the belief that coordinated water is needed for cleavage. An aqua ligand may be a labile leaving group that facilitates chelation or a nucleophile available for intramolecular attack. The latter mechanism may be favorable because the longer side chain of methionine (x=2) in AcMet-Gly is unsuitable for chelation but suitable for delivery of a water molecule to the peptide bond. This mechanism is helped also by the lability of aqua ligands coordinated to palladium-(II).

All publications and patents cited hereinabove are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

What is claimed is:

1. A method for peptide cleavage comprising reacting a peptide comprising a subunit of the formula (I):

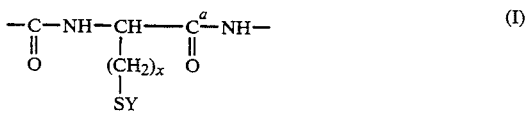

wherein x is 1 or 2 and Y is H or (C₁-C₄)alkyl; is treated in an aqueous medium with an amount of a tetracoordinate Pd(II) complex, wherein said complex comprises four chloro or 1-3 H₂O ligands, which complex is effective to bind to the SY unit of subunit (I) and to hydrolyze the amide bond designated a, proximal to the carboxy terminus of said subunit.

2. The method of claim 1 wherein x=1.
3. The method of claim 1 where Y=H.
4. The method of claim 1 wherein x=2.
5. The method of claim 4 wherein Y=H.
6. The method of claim 4 wherein Y=CH₃.
7. The method of claim 1 wherein the peptide is treated with a tetracoordinate Pd(II) complex.
8. The method of claim 1 wherein the complex comprises a ligand selected from the group consisting of H₂N(CH₂)₂-NH₂ ("en"), bipyridine ("bpy"), 1,5-dithiacyclooctane ("dtco") or hydroxyl ("OH").
9. The method of claim 8 wherein the complex is [Pd(H₂O)₃OH]⁺.
10. The method of claim 8 wherein the complex further comprises two H₂O ligands.
11. The method of claim 10 wherein the complex is cis-[M(en)(H₂O)₂]⁺² wherein M is Pd.
12. The method of claim 10 wherein the complex is cis-[Pd-(bpy)(H₂O)₂]⁺².

13. The method of claim 10 wherein the complex is cis-[Pd-(dtco)(H$_2$O)$_2$]$^{+2}$.

14. The method of claim 1 wherein the complex is [PdCl$_4$]$^{-2}$.

15. The method of claim 1 wherein the mole ratio of the Pd(II) complex to the subunit of formula I is about 1:1.

16. The method of claim 1 wherein the peptide comprises more than one subunit of the formula I and the amount of the [Pt(II) Pd(II) complex is effective to promote the hydrolysis of at least one of the subnit amide bonds proximal to the carboxy terminus of the subunit.

* * * * *

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i i ) MOLECULE TYPE: peptide ( v i ) ORIGINAL SOURCE:
( A ) ORGANISM: Gastric-related tetrapeptide ( x i ) SEQUENCE DESCRIPTION: SEQ ID NO:1:

Trp Met Asp Phe
1

UNITED STATES PATENT AND TRADEMARK OFFICE
CERTIFICATE OF CORRECTION

PATENT NO. : 5,352,771
DATED : October 4, 1994
INVENTOR(S) : Nenad M. Kostic et al.

It is certified that error appears in the above-indentified patent and that said Letters Patent is hereby corrected as shown below:

Column 8 Line 21 "C10$_4$δ=90" should read -- C10$_4$, e=90-- therefor.

Column 8 Line 21, "M$^{-1}$ cm$^{31-1}$ at" should read --M$^{-1}$cm$^{-1}$ at-- therefor.

Signed and Sealed this

Twenty-seventh Day of August, 1996

Attest:

BRUCE LEHMAN

*Attesting Officer*     *Commissioner of Patents and Trademarks*